United States Patent
Bornzin et al.

(10) Patent No.: US 9,302,112 B2
(45) Date of Patent: Apr. 5, 2016

(54) METHOD AND SYSTEM FOR NON-LINEAR FEEDBACK CONTROL OF SPINAL CORD STIMULATION

(71) Applicant: Pacesetter, Inc., Sunnyvale, CA (US)

(72) Inventors: Gene A. Bornzin, Simi Valley, CA (US); Edward Karst, Los Angeles, CA (US); Alexander Kent, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 21 days.

(21) Appl. No.: 14/304,615

(22) Filed: Jun. 13, 2014

(65) Prior Publication Data
US 2015/0360031 A1    Dec. 17, 2015

(51) Int. Cl.
*A61N 1/36*    (2006.01)

(52) U.S. Cl.
CPC ........ *A61N 1/36139* (2013.01); *A61N 1/36071* (2013.01)

(58) Field of Classification Search
CPC ................ A61N 1/36139; A61N 1/36071
See application file for complete search history.

(56) References Cited

U.S. PATENT DOCUMENTS

2006/0224187 A1*  10/2006  Bradley ............ A61N 1/36071
                                                  607/2

FOREIGN PATENT DOCUMENTS

WO    WO 2012/155188    11/2012

* cited by examiner

*Primary Examiner* — Rex R Holmes
(74) *Attorney, Agent, or Firm* — Theresa A. Raymer

(57) ABSTRACT

A system of non-linear feedback control for spinal cord stimulation is provided. The system comprises a lead adapted to be implanted within an epidural space of a dorsal column of a patients spine, and a pulse generator (PG) electrically coupled to the lead. The PG is configured to deliver spinal cord stimulation (SCS) therapy. The system also comprises a sensing circuitry configured to sense an evoked compound action potential (ECAP) response that propagates along the neural pathway. The system also comprises a processor programmed to operation, in response to instructions stored on a non-transient computer-readable medium, to obtain a baseline ECAP response when the lead and spinal cord tissue properties are in baseline states; analyze ECAP responses relative to the baseline ECAP response to obtain an ECAP feedback difference indicative of a change in at least one of the baseline state of the lead and the baseline state of the spinal cord tissue properties. The processor is also programmed to adjust an SCS therapy based on the ECAP feedback.

22 Claims, 8 Drawing Sheets

METHOD AND SYSTEM FOR NON-LINEAR FEEDBACK CONTROL OF SPINAL CORD STIMULATION

BACKGROUND OF THE INVENTION

Embodiments of the present invention generally relate to spinal cord stimulation and more particularly to feedback control of stimulation as a lead moves with respect to the dorsal column of the spinal cord.

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can mask certain types of pain transmitted from regions of the body associated with the stimulated nerve tissue. Applying electrical energy to the spinal cord associated with regions of the body afflicted with chronic pain can induce "paresthesia" (a subjective sensation of numbness or tingling) in the afflicted bodily regions. Paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Spinal cord stimulation (SCS) is an effective therapy for chronic, intractable pain, and may be beneficial in treating other diseases including heart failure and vascular disease.

The SCS lead can shift, for example by up to 3 mm, relative to the spinal cord when a patient moves between postures, such as from a supine to prone position. Further, lead migration away from the implantation site can occur even in the absence of patient movement. When the lead shifts closer to or further from the spinal cord, an amount of stimulation energy that reaches the spinal cord increases or decreases, respectively, from a given initial stimulation amount of energy delivered from the lead. When the lead shifts closer to the spinal cord, the amount of stimulation energy that reaches the spinal cord increases. The increase may result in over-stimulation that may generate side effects that are uncomfortable for the patient, and may increase the likelihood of tissue damage due to high charge injection. Conversely, when the lead shifts away from the spinal cord, the amount of stimulation energy that reaches the spinal cord decreases. The decrease may result in under-stimulation that may cause a reduction or loss of paresthesia coverage and therapy for pain reduction. In addition to changes in lead-spinal cord distance, these shifts can produce changes in the electrical impedance of the surrounding tissue, which may shunt current towards or away from the targeted spinal cord region and change stimulation thresholds. Automatic adjustment of stimulation parameters, such as amplitude or pulse width, may compensate for these changes.

Evoked compound action potentials (ECAPs) are generated in the extracellular space by synchronous activation of a large number of nerve fibers in the dorsal column, and are sufficiently large to be recorded from electrodes in close proximity to the neurons on a SCS lead during stimulation. The ECAP signal may provide a suitable feedback signal for parameter adjustment across different lead positions, because the sensed ECAP signal amplitude is linearly related to the percentage of pain coverage with variation in stimulation current. It has been proposed to use the ECAP signal as a feedback signal in SCS.

However, the thus proposed method requires a preliminary training period to establish a "therapy map," in which the ECAP signal amplitude is measured across a large number of stimulation amplitudes and patient postures. The training period is both time-consuming and incorrectly assumes a linear relationship in sensed ECAP signal amplitude between different lead-spinal cord distances.

A need remains for improved methods and systems for controlling spinal cord stimulation.

SUMMARY

In accordance with one embodiment, a system is provided of feedback control for spinal cord stimulation. The system comprises a lead adapted to be implanted within an epidural space of a patient's spine near the dorsal column, and a pulse generator (PG) electrically coupled to the lead, the PG configured to deliver spinal cord stimulation (SCS) therapy. The system also comprises a sensing circuitry configured to sense an evoked compound action potential (ECAP) response that propagates along the neural pathway. The system also comprises a processor programmed to operation, in response to instructions stored on a non-transient computer-readable medium, to obtain a baseline ECAP response when the lead and spinal cord tissue properties are in baseline states; analyze ECAP responses relative to the baseline ECAP response to obtain an ECAP feedback difference indicative of a change in at least one of the baseline state of the lead and the baseline state of the spinal cord tissue properties; and adjust an SCS therapy based on the ECAP feedback difference.

Optionally, the system may comprise a lead having one or more electrodes that represent a sensing electrode and a stimulation electrode, the sensing electrode coupled to the sensing circuitry, the stimulation electrode coupled to the PG, the sensing and stimulation electrodes including one of a common electrode, distinct electrodes and partially overlapping electrodes. Alternatively, the system may comprise a processor configured to undergo an initial calibration process by tuning a constant that includes at least one of the baseline ECAP response, a baseline SCS therapy, and the baseline CFD, associated with a therapeutic level sufficient to create a select patient paresthesia coverage.

Alternatively, the system may comprise a processor configured to determine, as part of a baseline SCS therapy, electrode(s) to deliver SCS therapy, a pulse sequence in the SCS therapy, and a morphology for the pulses within the pulse sequence, the morphology including at least one of an amplitude of pulses, pulse width, a number of pulses in a series of pulses, and a pulse delivery rate. Optionally, the system may comprise the SCS therapy creating current flux density (CFD) at nerve fibers within a target tissue site along the neural pathway, and a level of the CFD induced onto the nerve fibers at the target tissue site, with the level based in part on at least one of i) a distance between the nerve fibers and excitation electrodes, or ii) a level of energy emitted at the excitation electrode, the processor configured to utilize the ECAP feedback difference to adjust the SCS therapy to maintain a select CFD level within a select limit of the baseline CFD at the target tissue site.

Optionally, the system may be configured wherein a linear relation exists between an amount of current flux density, Jstim, experienced by a bundle of nerve fibers, and a level of an ECAP response, Vecap, that is sensed along a common bundle of nerve fibers, the processor configured to adjust the SCS therapy based on the linear relation. Alternatively, the system may be configured wherein, when the lead shifts in a radial direction toward or away from the spinal cord, a current flux density at the target tissue site changes and in response thereto the ECAP response changes, the processor configured to utilize the change in the ECAP response to calculate information representative of a new distance between the target tissue site to be excited and the electrode. Optionally, the system may be configured wherein the processor is configured to adjust a stimulation parameter of the SCS therapy in a non-linear relation to changes in the ECAP responses sensed. Alternatively, the system may be configured wherein the processor is configured to adjust a gain of the SCS therapy in accordance with a non-linear relation relative to changes in the baseline state of at least one of the lead or spinal cord tissue.

Alternatively, the system may be configured wherein the baseline ECAP response is induced by a baseline current flux density when the lead is in the baseline state, the baseline state representing a baseline distance between the lead and the dorsal column. Optionally, the system may be configured wherein the change in the spinal cord tissue (SCT) properties represents a change in at least one of i) electrical conductivity, ii) thickness of the cerebral spinal fluid layer, iii) fluid status within the cerebral spinal fluid, or iv) tissue composition between lead and spinal column.

Optionally, the system may be configured wherein the processor is programmed to adjust the SCS therapy such that a current flux density (CFD) at the target tissue site remains within a select CFD limit relative to a baseline CFD associated with the SCS therapy delivered when the lead is in the baseline state.

In accordance with another embodiment, a method is provided which is configured to provide feedback control for spinal cord stimulation from a lead adapted to be implanted within an epidural space of a dorsal column of a patient's spine. The method comprises delivering spinal cord stimulation (SCS) therapy to a target tissue site. The method also comprises sensing an evoked compound action potential (ECAP) response that propagates along the neural pathway; obtaining a baseline ECAP response when the lead and spinal cord tissue properties are in a baseline state; and analyzing ECAP responses relative to the baseline ECAP response to obtain an ECAP feedback difference indicative of a change in at least one of the baseline state of the lead and the baseline state of the spinal cord tissue properties. The method also comprises adjusting an SCS therapy based on the ECAP feedback difference.

Optionally, the method may further comprise performing an initial calibration process by tuning a constant that includes at least one of the baseline ECAP response, a baseline SCS therapy, and the baseline CFD, associated with a therapeutic level sufficient to create a select patient paresthesia coverage. Alternatively, the method may further comprise determining, as part of a baseline SCS therapy, electrode(s) to deliver SCS therapy, a pulse sequence in the SCS therapy, and a morphology for the pulses within the pulse sequence, the morphology including at least one of an amplitude of pulses, pulse width, a number of pulses in a series of pulses, and a pulse delivery rate.

Alternatively, the method may be configured wherein the SCS therapy creates current flux density (CFD) at nerve fibers within a target tissue site along the neural pathway, and wherein a level of the CFD induced onto the nerve fibers at the target tissue site is based in part on at least one of i) a distance between the nerve fibers and excitation electrodes, or ii) a level of energy emitted at the excitation electrode, the analyzing and adjusting operations using the ECAP feedback difference to adjust the SCS therapy to maintain a select CFD level within a select limit of the baseline CFD at the target tissue site. Optionally, the method may be configured wherein a linear relation exists between an amount of current flux density, Jstim, experienced by a bundle of nerve fibers, and a level of an ECAP response, Vecap, that is sensed along a common bundle of nerve fibers, the adjusting operation adjusting the SCS therapy based on the linear relation.

Optionally, the method may be configured wherein, when the lead shifts in a radial direction toward or away from the spinal cord, the CFD at the target tissue site changes and in response thereto the ECAP response changes, the analyzing operation utilizing the change in the ECAP response to calculate information representative of a new distance between the target tissue site to be excited and the electrode. Alternatively, the method may be configured wherein the adjusting operation adjusts a stimulation parameter of the SCS therapy in a non-linear relation to changes in the ECAP responses sensed. Optionally, the method may be configured wherein the adjusting operation adjusts a gain in accordance with a non-linear relation relative to changes in the baseline state of at least one of the lead or spinal cord tissue.

Alternatively, the method may be configured wherein the baseline state for the lead represents a baseline distance between the lead and the dorsal column. Optionally, the method may be configured wherein the adjusting operation adjusts the SCS therapy such that a therapy current flux density (CFD) at the target tissue site remains within a select CFD limit relative to a baseline CFD when the lead and spinal cord tissue properties are in the baseline states.

DETAILED DESCRIPTION

Embodiments herein provide an ECAP-based feedback process for automatically adjusting SCS therapy amplitude and/or pulse width in response to changes in lead position, and consequent alteration of the stimulation threshold. Embodiments herein describe a process that accounts for the relationships between the stimulation electrode-to-spinal cord distance and the sensing electrode-to-spinal cord distance. The process incorporates electrical impedance measurements to adjust stimulation in response to changes in the electrical impedance of surrounding body tissue or fluid in the spinal canal, which can cause shunting of stimulation current. Embodiments herein improve the safety and efficacy of SCS by compensating for changes in stimulation thresholds and reducing variability in paresthesia coverage and pain reduction as the patient moves between postures or the lead migrates from the implantation site.

Figure 1:
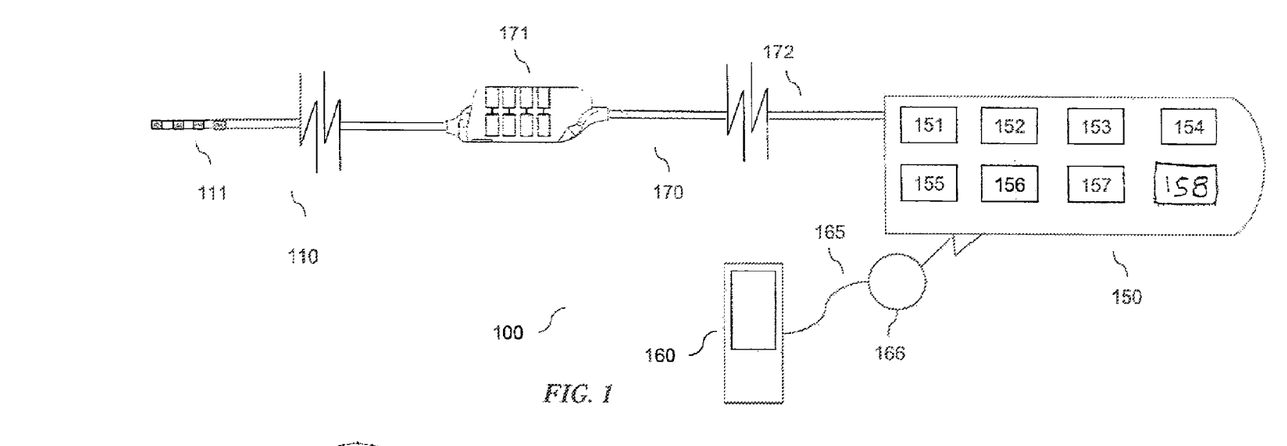
FIG. 1 depicts a stimulation system according to some representative embodiments.

FIG. 1 depicts a stimulation system 100 that generates electrical pulses for application to tissue of a patient according to an embodiment. For example, system 100 may be adapted to stimulate spinal cord tissue, peripheral nerve tissue, deep brain tissue, cortical tissue, cardiac tissue, digestive tissue, pelvic floor tissue, or any other suitable tissue within a patient's body.

System 100 includes an implantable pulse generator 150 that is adapted to generate electrical pulses for application to tissue of a patient. Implantable pulse generator 150 typically comprises a metallic housing that encloses controller 151, pulse generating circuitry 150, charging coil battery 153, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the pulse generator 150 for execution by the microcontroller or processor to control the various components of the device. The controller 151, PG circuitry 150, switching circuitry 157 and sensing circuitry 158 operate as explained below in connection with FIGS. 3-10 to implement embodiments herein.

The IPG 150 provides non-linear feedback control for spinal cord stimulation. The lead 110 is adapted to be implanted within an epidural space of a dorsal column of a patient's spine. The pulse generator (PG) circuitry 150 is electrically coupled to the lead 110. The PG 150 is configured to deliver spinal cord stimulation (SCS) therapy that creates current flux density (CFD) at nerve fibers within a target tissue site along the neural pathway. Sensing circuitry 158 is coupled through the switching circuitry 157 to one or more electrodes 121. The sensing circuitry 158 is configured to sense an evoked compound action potential (ECAP) response that propagates along the neural pathway, the ECAP response evoked by the CFD. The controller includes a processor programmed to operation, in response to instructions stored on a non-transient computer-readable medium, to: i) obtain a baseline ECAP response induced by a baseline CFD when the lead is at a baseline distance from the dorsal column; ii) analyze ECAP responses relative to the baseline ECAP response to obtain an ECAP feedback difference indicative of a change in a distance between the lead and the dorsal column; and iii) adjust an SCS therapy based on the ECAP feedback difference such that a therapy CFD at the target tissue site remains within a select CFD limit relative to the baseline CFD.

The leads 110 have one or more electrodes that represent a sensing electrode and a stimulation electrode. The sensing electrode 121 is coupled to the sensing circuitry. The stimulation electrode 121 is coupled to the PG 150. The sensing and stimulation electrodes 121 including one of a common electrode, distinct electrodes and partially overlapping electrodes. The controller 152 is configured to undergo an initial calibration process by tuning a constant that includes at least one of the baseline ECAP response, a baseline SCS therapy, and the baseline CFD, associated with a therapeutic level sufficient to create a select patient paresthesia coverage. The controller 152 is configured to determine, as part of a baseline SCS therapy, electrode(s) to deliver SCS therapy, a pulse sequence in the SCS therapy, and a morphology for the pulses within the pulse sequence, the morphology including at least one of an amplitude of pulses, pulse width, a number of pulses in a series of pulses, and a pulse delivery rate. A level of the CFD induced onto the nerve fibers at the target tissue site may be based in part on at least one of i) a distance between the nerve fibers and excitation electrodes, or ii) a level of energy emitted at the excitation electrode, the processor configured to utilize the ECAP feedback difference to adjust the SCS therapy to maintain a select CFD level within a select limit of the baseline CFD at the target tissue site.

A linear relation exists between an amount of current flux density, Jstim, experienced by a bundle of nerve fibers, and a level of an ECAP response, Vecap, that is sensed along a common bundle of nerve fibers, the processor configured to adjust the SCS therapy based on the linear relation. When the lead shifts in a radial direction toward or away from the spinal cord, the CFD at the target tissue site changes and in response thereto the ECAP response changes, the processor configured to utilize the change in the ECAP response to calculate information representative of a new distance between the target tissue site to be excited and the electrode. The controller 152 is configured to adjust a gain of the SCS therapy in a non-linear relation to changes in the ECAP responses sensed. The controller 152 is configured to adjust the gain in accordance with a non-linear relation relative to changes in the ECAP responses sensed.

Pulse generator 150 may comprise a separate or an attached extension component 170. If extension component 170 is a separate component, extension component 170 may connect with the "header" portion of pulse generator 150 as is known in the art. If extension component 170 is integrated with pulse generator 150, internal electrical connections may be made through respective conductive components. Within pulse generator 150, electrical pulses are generated by pulse generating circuitry 150 and are provided to switching circuitry 157. The switching circuit connects to outputs of pulse generator 150. Electrical connectors (e.g., "Bal-Seal" connectors) within connector portion 171 of extension component 170 or within the IPG header may be employed to conduct the stimulation pulses. The terminals of one or more stimulation leads 110 are inserted within connector portion 171 or within the IPG header for electrical connection with respective connectors. Thereby, the pulses originating from pulse generator 150 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may comprise a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2A:
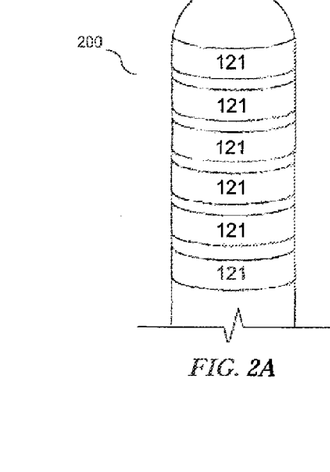
FIGS. 2A-2C respectively depict stimulation portions for inclusion at the distal end of a lead according to some representative embodiments.
Figure 2B:
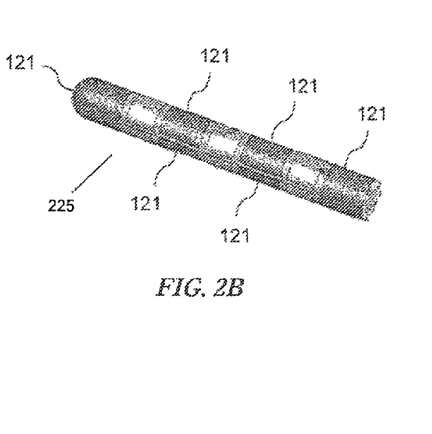
Figure 2C:
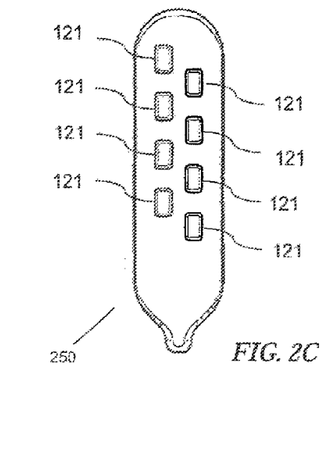

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

The ability to elongate at relatively low forces may present one or more advantages for implantation in a patient. For example, as a patient changes posture (e.g., "bends" the patient's back), the distance from the implanted pulse generator to the stimulation target location changes. The lead body may elongate in response to such changes in posture without damaging the conductors of the lead body or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate responsive to movement of the patient's neck, certain lead bodies according to some embodiments are better adapted for such implants than some other known lead body designs. Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference.

Controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 153 by charging circuitry 154. Charging circuitry 154 may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 160 may permit operation of IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Figure 3:
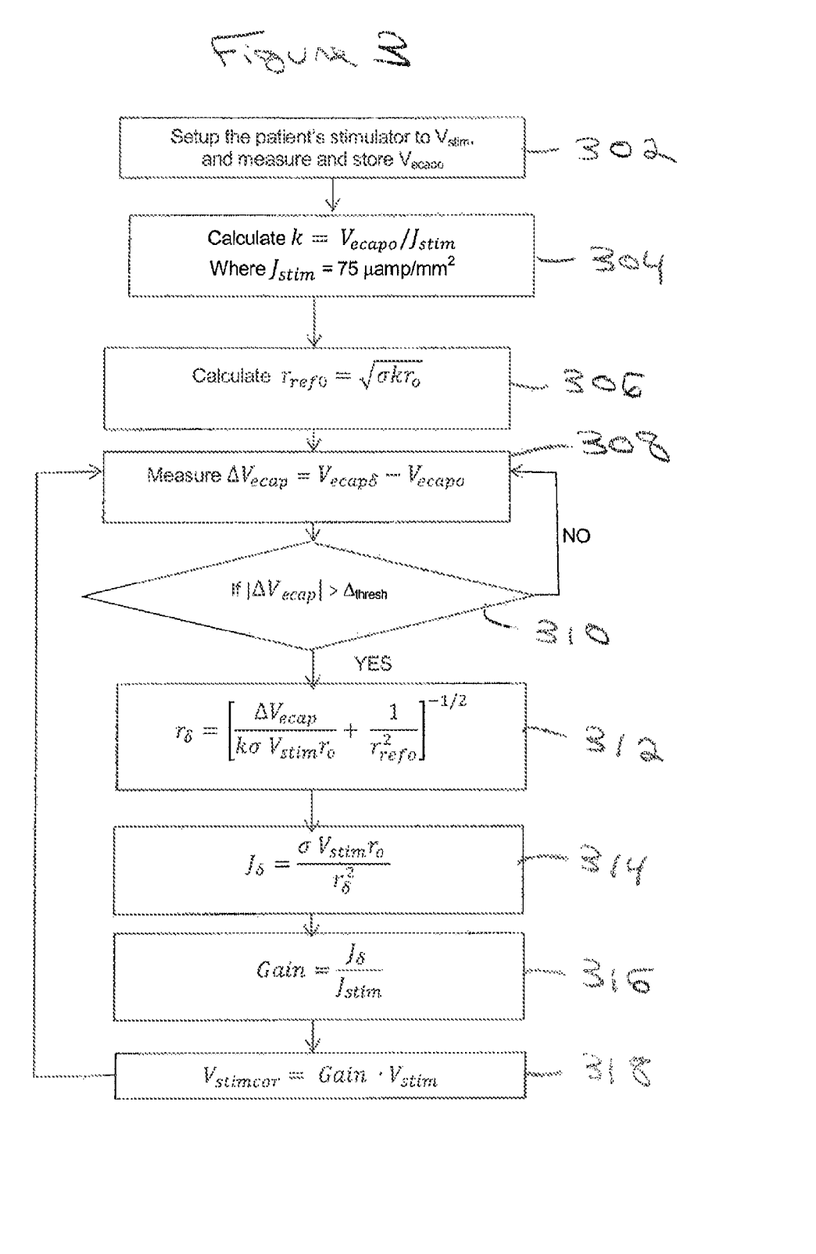
FIG. 3 illustrates a process to control of an SCS therapy that performs non-linear feedback to maintain a resultant excitation energy that is experienced at a target tissue site within a select limit or range in accordance with an embodiment.

FIG. 3 illustrates a process to control of an SCS therapy that performs non-linear feedback to maintain a resultant excitation energy that is experienced at a target tissue site within a select limit or range. The resultant excitation energy may be characterized as a current flux density experienced at the target tissue site. The method adjusts spinal cord stimulation parameters in response to changes in lead/electrode position in order to maintain constant (or range bound) current flux density. The change in electrode position is indirectly monitored through a sensed feedback signal. The feedback signal constitutes recorded evoked compound action potential (ECAP) response that occurs within the nerve fiber in response to excitation of the nerve fiber. The change in the ECAP response represents an estimate of a relative positional change of the excitation and sensing electrode(s), relative to nerve fiber at a target tissue site. The ECAP response is proportional to an actual current flux density that is present at the target tissue site (as compared to a desired or baseline current flux density that was previously determined as an appropriate amount to achieve a select amount of paresthesia at a corresponding select coverage zone).

The method and system compensate for estimated changes in current flux density by adjusting the stimulus parameters automatically. The ECAP responses may be recorded from the same electrode(s) as used for stimulation, immediately after delivery of stimulation pulses. A switching circuit is used to selectively connect the electrode(s) to an SCS therapy delivery pulse generator and then to sensing circuitry. Optionally, the electrodes used for sensing may be distinct from, and adjacent to, the stimulation electrodes. The sensing circuitry may be operated to measure continuously, periodically, or triggered ECAP responses. When different electrodes are used for sensing ECAP signals and for delivering SCS therapy, the sensing and therapy electrodes are positioned on the lead such that similar changes in the spacing or orientation between the lead and the dorsal column of the spinal cord occur for the stimulation and sensing electrodes.

In yet another embodiment, the sensing electrodes may be located on the same lead or on a different lead than the stimulation electrodes such that the sensing electrodes are distinct from and spaced relatively far from the stimulating electrodes. The sensing and stimulation electrodes may be spaced relatively far apart so that dispersion of activation times along distinct types of nerve fibers is increased while activation along the same type of neuron remains nearly simultaneous, thereby enabling a higher degree of accuracy and discrimination between types of excited fibers during the sensing operation.

Beginning at 302, one or more leads are implanted and connected to an SCS device or programmer. A physician, the patient or other user performs an initial test process to calibrate the system by tuning SCS parameters, such as the baseline ECAP response $V_{ecapo}$, the baseline excitation voltage $V_{stim}$, the baseline current flux density $J_{stim}$, and the like.

To tune SCS parameters, the physician and patient determine a baseline stimulation or therapeutic level (baseline SCS therapy) sufficient to treat or titrate the patient's paresthesia coverage. The process for determining the baseline stimulation may include determining which electrode(s) should be used to deliver SCS therapy, which pulse sequence to include in the SCS therapy, which morphology to use for the pulses within the pulse sequence, and the like. The morphology includes the amplitude(s) of the pulses, the pulse widths, the number of pulses in a series, the rate at which pulses are delivered and the like. The physician adjusts the parameters for the SCS therapy until achieving a desired amount of paresthesia at the select coverage zone. Once the baseline stimulation $V_{stim}$ is found, the SCS parameters associated with the baseline stimulation are stored in a data storage. The information associated with the baseline stimulation $V_{stim}$ includes a corresponding resultant excitation energy experienced at a target tissue site (e.g., a region of the nerve fiber within the dorsal column proximate to the excitation electrode). The information may include a select limit or range for the resultant excitation energy. By way of example, the resultant excitation energy may be characterized as a baseline current flux density at the nerve fibers for the portion of the dorsal column at the target tissue site proximate to the excitation electrodes. The level of the current flux density induced onto, or experienced by, the nerve fibers is dependent in part on the distance between the nerve fibers and the excitation electrodes. The level of the current flux density induced onto, or experienced by, the nerve fibers is also dependent on a level of energy emitted at the surface of the electrode, such as the voltage potential at the electrode. The process for determining the resultant excitation energy level in general involves determining an amount of current flux density to induce into a select thickness of nerve fibers within the excitation zone. For example, it may be determined that nerve fibers, within a thickness of approximately 2 mm, are to be excited at a select current flux density. Optionally, it may be determined to excite nerve fibers at a select depth within the dorsal column at the select current flux density.

In SCS devices that deliver an SCS therapy based on stimulation voltage, $V_{stim}$, the stimulation voltage amplitude $V_{stim}$ represents a parameter that is adjusted in accordance with embodiments herein to maintain a select current flux density at the target tissue site. It is recognized that the present description describes a stimulation voltage for ease of understanding. Optionally, the SCS device may be implemented as a constant-current stimulation system, wherein the SCS device adjusts the current delivered in connection with stimulation to maintain the select current flux density at the target tissue site. When a constant current SCS device is implemented, the processes and calculations described herein could be equivalently represented using stimulation current $I_{stim}$, and the like.

Remaining as 302 in FIG. 3, the method measures one or more ECAP responses. One or more electrodes on the lead are used to sense or measure the ECAP responses to generate an ECAP signal. The ECAP signal may be measured as a voltage potential, $V_{ecapo}$, which represents the ECAP voltage amplitude sensed by the sensing electrodes while the sensing electrodes are spaced an initial distance from the dorsal column (e.g., at the initial lead position). The ECAP signal (voltage), $V_{ecapo}$, is stored in the data storage.

At 304, the method calculates a transfer factor that represents a constant relation between the amount of excitation energy experienced at the target tissue site, $J_{stim}$, and an associated measured ECAP response, $V_{ecapo}$. The transfer factor may be referred to as an excitation-to-response (ETR) transfer factor. To calculate the ETR transfer factor, the method first determines the resultant excitation energy (REE) that is experienced at the target tissue site. The REE may be characterized as a current flux density (CFD), $J_{stim}$. The CFD may be predetermined and entered by a physician or other user. Optionally, the CFD may be measured, or calculated.

A linear relation exists between a level of current flux density, $J_{stim}$, experienced by a bundle of nerve fibers, and a level of an ECAP response, $V_{ecap}$, that is sensed along the same bundle of nerve fibers. As the current flux density, $J_{stim}$, increases, the ECAP response, $V_{ecap}$, similarly increases. The linear relationship between the sensed ECAP response, $V_{ecapo}$, at a sensing region along the neural pathway and the stimulation current flux density $J_{stim}$ holds because as the current flux density $J_{stim}$ increases the number of recruited neurons (or nerve fibers) increases. The excited nerve fibers at least partially surround the sensing electrode and are in a conductive medium (e.g., tissue and cerebro-spinal fluid). Therefore, the potential sensed at the surface of a sensing electrode closely matches the potential in the area around the excited neurons.

Figure 4A:
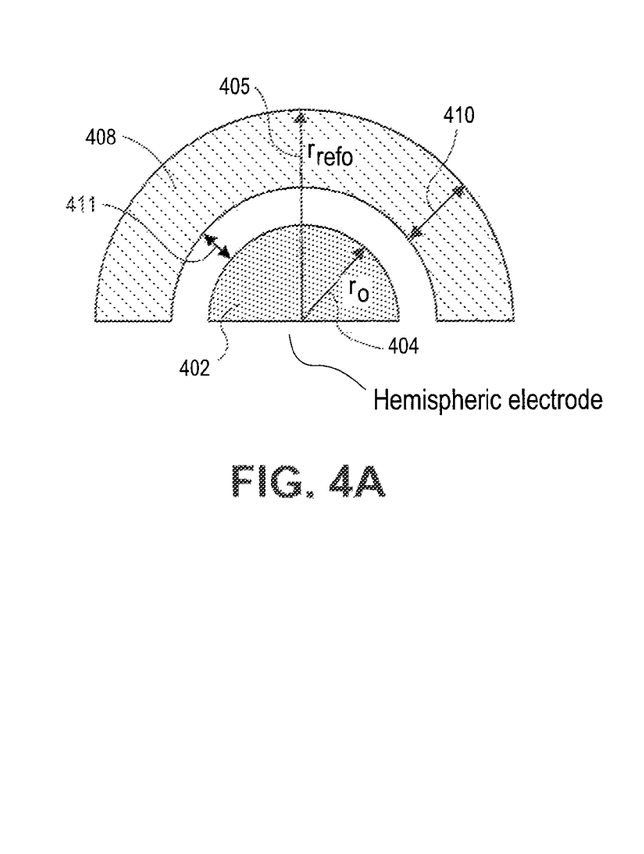
FIGS. 4A and 4B illustrate a graphical representation of a portion of an excitation and/or sensing electrode and exemplary ranges in which nerve fibers may be located at a time of lead implant when the baseline stimulation parameters are determined (FIG. 4A) and post implant/post calibration (FIG. 4B) in accordance with an embodiment.
Figure 4B:
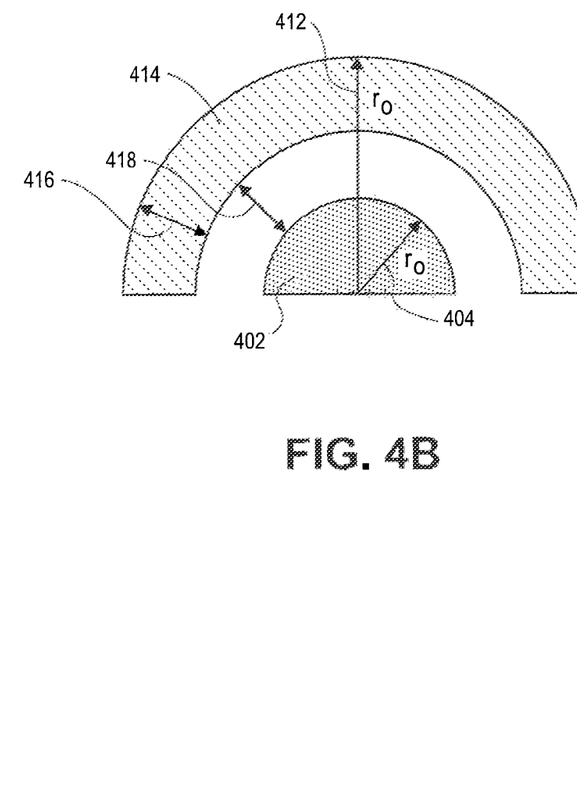

FIGS. 4A and 4B illustrate a graphical representation of a portion of an excitation and/or sensing electrode and exemplary ranges in which nerve fibers may be located at a time of lead implant when the baseline stimulation parameters are determined (FIG. 4A) and post implant/post calibration (FIG. 4B). The stimulation electrode 402 has a radius of 404, $r_0$. The electrode 402 delivers stimulation energy. The stimulation energy propagates outward from the electrode 402 and exhibits an amount of current flux density that varies based upon a distance from the electrode 402. For example, the stimulation energy exhibits a greater level of current flux density in a region immediately adjacent the electrode 402, with the level of current flux density decreasing at distances further and further from the electrode 402. In FIG. 4A, the region 408 represents the location of the nerve fibers of interest when the baseline stimulation is determined. The region 408 has an associated current flux density, Jstim, when the target tissue site is within a distance 406 $r_{ref}$ from the center of the electrode 402. In FIG. 4A, the stimulation electrode 402, may be conceptually represented as a hemisphere with radius $r_o$. The reference distance, $r_{ref}$ corresponds to the distance from a center of the electrode to a distal perimeter of the target tissue site. The target tissue site has a thickness 410 and is spaced a distance 411 from an edge of the electrode 402. The reference distance 406, $r_{ref0}$, may be computed from two factors, the stimulation voltage, $V_{stim}$, and the current flux density $J_{stim}$, at the nerve fibers that are targeted for stimulation. As an example, the current flux density, $J_{stim}$, may be approximately 75 $\mu A/mm^2$, while the thickness 410 of the nerve fiber to be stimulated may be approximately 2 mm.

FIG. 4B illustrates the electrode 402 at a later point in time, after implant, when the lead has shifted within the epidural space away from the dorsal column. In FIG. 4B, the target tissue site is located in a region 414 having a thickness 416 and spaced a distance 418 away from an edge of the electrode 402. The electrode 402 has moved some distance 412 away from the tissue (nerve fibers), although the thickness 416 of excited tissue 414 that is desirable to be excited for paresthesia remains the same (e.g., 2 mm). For example, when the lead is in a dorsal-ventral location, over time as the patient moves, the lead shifts. The lead floats in the epidural space outside the fluid layer. The lead may experience dorsal migration (e.g., away from the spinal column), ventral migration (e.g., toward the spinal column), caudal migration (e.g., away from the head), or cranial migration (e.g., toward the head). Each type of migration changes the distance between the target tissue site and the excitation/sensing electrodes.

The hemispheric solution illustrated in FIGS. 4A and 4B recognizes that the sensed ECAP response voltage amplitude ($V_{ecapo}$), that is sensed for a collection of nerve fibers, is proportional to the current flux density, $J_{stim}$, that excites the same collection of nerve fibers. Therefore, the following relationship remains true, where k represents a constant transfer factor:

$$V_{ecapo} = k \cdot J_{stim}, \qquad \text{Equation 1.}$$

Equation 1 can be rewritten as follows to solve for the constant transfer factor k:

$$k = V_{ecapo}/J_{stim} \qquad \text{Equation 2.}$$

At 306, the method then calculates the initial distance $r_{refo}$ between the electrodes of the lead and target tissue site of the dorsal column of the spinal cord. For example, the initial distance $r_{refo}$ may represent the distance between a boundary of the dorsal column and a reference point or surface of the electrodes or lead. In a clinical setting, the initial distance $r_{refo}$ may be measured using post-implant x-ray, from a sensor attached to the lead such as an ultrasonic or optical sensor, or during lead implantation from an implant tool. Following implant and establishment of the baseline stimulation level, when the electrodes shift such that the distance is less than the baseline distance $r_{refo}$, more nerve fibers are excited, than a desired amount. The increase in the number of excited nerve fibers occurs because the new current flux density exceeds the baseline current flux density, $J_{stim}$. Conversely, when the electrodes shift such that the electrode-to-spinal column distance is greater than the baseline distance $r_{frefo}$, fewer nerve fibers are excited, than the desired amount. The decrease in the number of excited nerve fibers occurs because the new current flux density falls below the baseline current flux density, $J_{stim}$.

The baseline current flux density $J_{stim}$ can be characterized based on the baseline stimulation voltage, $V_{stim}$, the radius of the electrode, $r_o$, and the reference distance $r_{ref}$ from the center of the electrode to the distal edge of the target tissue site, based on the following equation, where sigma, σ, represents tissue conductivity:

$$J_{stim} = \frac{\sigma V_{stim} r_o}{r_{ref}^2}. \qquad \text{Equation 3}$$

By way of example, measurement of electrical impedance from the lead could provide a technique for determining an appropriate value for tissue conductivity (σ). The electrical impedance may be measured between two contacts, such as the stimulating electrode and a distant return electrode, the stimulating and ECAP sensing electrodes, or some other combination. This measurement may be performed periodically, or in response to a change in the ECAP response. In the foregoing example, impedance is first measured at baseline with the lead placed on the spinal cord ($Z_{0,SC}$) and away from the spinal cord within the cerebro-spinal fluid ($Z_{0,CSF}$). Subsequent impedance measurements ($Z_1$) can be compared with these baseline measurements, to determine if the lead is near the spinal cord ($Z_1 \approx Z_{0,SC}$), within the cerebro-spinal fluid ($Z_1 \approx Z_{0,CSF}$), or near other body tissues (i.e. bone). These calculations (not shown) could also be used to estimate the change in electrode position, $r_{ref0}$.

Additionally or alternatively, the impedance measurement could be used to adjust stimulation in response to tissue overgrowth on the lead following implantation. For example, in certain instances, encapsulation tissue forms between the electrode surface and spinal cord, thereby increasing the impedance in the peri-electrode space and generating higher stimulus thresholds for neural activation. Impedance measurements could be used to indicate the presence and extent of the encapsulation, through comparison to baseline measurements. For example, the conductivity of the encapsulation tissue could be on the order of 235 μsiemens/mm with a thickness in the range of 0.2 to 0.8 mm. The corresponding stimulation parameter adjustments could be performed in the presence or absence of lead movement.

In addition to an impedance measurement, or alternatively, a sensor technology, such as a piezoelectric material, could be used for ultrasonic measurement of tissue encapsulation and determination of the distance from electrode to the spinal cord. In addition or alternatively, an optical sensor may be used with one or more wavelengths of visible or near-infrared light to distinguish encapsulating tissue, cerebro-spinal fluid and the dorsal column. For example, cerebro-spinal fluid is largely transparent at red wavelengths around 700 nm, but opaque at near infrared wavelengths around 1300 nm. A combination of two LEDs or laser diodes and a single photodetector would be able to distinguish photometrically the distance to the dorsal column.

Equation 3 may be solved for the reference distance $r_{refo}$ as follows:

$$r_{refo} = \sqrt{\frac{\sigma V_{stim} r_o}{J_{stim}}} = \sqrt{\sigma k r_o}. \qquad \text{Equation 4}$$

At 306, the method applies Equation 4 to calculate the reference distance, $r_{refo}$, between a center of the electrode and a distal edge of the target tissue site, and associated with the baseline stimulation $V_{stim}$. If the electrode shifts in a radial direction (toward or away from the spinal cord), the current flux density at the target tissue site changes and similarly the ECAP response will change to a new or different ECAP response voltage $V_{ecap\delta}$. As explained herein, operations at 308-318 utilize the change in the ECAP response to calculate information representative of the new distance between the target tissue site to be excited and the electrode, $r_\delta$.

The method utilizes equations 2 and 3 above to first compute the baseline ECAP response (voltage amplitude) at the initial electrode position as follows:

$$V_{ecapo} = k \cdot \frac{\sigma V_{stim} r_o}{r_{refo}^2}. \qquad \text{Equation 5}$$

At 308, the method measures/senses a new ECAP response, $V_{ecap\delta}$. The new ECAP response $V_{ecap\delta}$ may be measured continuously, periodically, at select times, in response to certain conditions and the like. For example, a new ECAP response may be measured every hour, every time a motion sensor in the SCS device detects a change in orientation, at select times each day and the like. The method uses the difference between the baseline and new ECAP responses, $V_{ecap\delta} - V_{ecapo}$ to calculate a distance change, $r_\delta$. From equation 5, the new distance, $r_\delta$, between the electrode and the target tissue site can be calculated as follows:

$$V_{ecap\delta} = k \cdot \frac{\sigma V_{stim} r_o}{r_\delta^2}. \qquad \text{Equation 6}$$

The difference between equations 5 and 6 becomes:

$$V_{ecap\delta} - V_{ecapo} = \Delta V_{ecap} = k \cdot \sigma V_{stim} r_o \left[ \frac{1}{r_\delta^2} - \frac{1}{r_{refo}^2} \right]. \qquad \text{Equation 7}$$

At 310, the method determines whether the change in ECAP response is sufficient to exceed a threshold, $\Delta_{thresh}$, that warrants adjustment of the SCS therapy. When the ECAP response change falls below the threshold $\Delta_{thresh}$, flow moves back to 308 where the next new ECAP response is measured. Otherwise, flow moves to 312.

At 312, the change in distance $r_\delta$ is determined for the electrode to spinal cord distance. The distance change $r_\delta$ is calculated by solving Equation 7 for distance $r_\delta$. The method solves for the distance change, $r_\delta$ as follows:

$$r_\delta = \left[ \frac{\Delta V_{ecap}}{k\sigma V_{stim}r_o} + \frac{1}{r_{refo}^2} \right]^{-1/2}; \quad \text{Equation 8}$$

At 314, once the distance change $r_\delta$ between the electrode and the target tissue site is known, the method calculates an expected change in current flux density using the computed distance change, $r_\delta$, as follows:

$$J_\delta = \frac{\sigma V_{stim} r_o}{r_\delta^2}. \quad \text{Equation 9}$$

At 316, once the change in current flux density $J_\delta$ is known, the method then calculates a ratio between the baseline current flux density and the new current flux density as follows: By determining gain as a ratio of the baseline and new current flux densities, the method is able to determine a scale factor, the gain, by which the baseline stimulation should be scaled to a new level in order to adjust the current flux density from the new density $J_\delta$ back to the desired target level, $J_{stim}$:

$$\text{Gain} = \frac{J_\delta}{J_{stim}}. \quad \text{Equation 10}$$

At 318, the method applies the Gain to adjust the SCS therapy. Various stimulation parameters of the SCS therapy may be adjusted, by way of example only, by adjusting one or more of a pulse sequence in the SCS therapy, a morphology for the pulses within the pulse sequence, where the morphology includes one or more of an amplitude of pulses, pulse width, a number of pulses in a series of pulses, a pulse delivery rate and the like. For example, when the stimulation parameter to be adjusted represents stimulation level (e.g., pulse amplitude) the baseline stimulation $V_{stim}$ is used in order to calculate a corrected stimulation level ($V_{stimcor}$) that restores the current flux density from $J_\delta$ to the original level, $J_{stim}$. The corrected stimulation level is determined based on the following equation:

$$V_{stimcor} = \text{Gain} \cdot V_{stim} \quad \text{Equation 11.}$$

Optionally, the corrected stimulation level may represent an adjustment in the pulse width based on the gain, such as $PW_{stimcor} = \text{Gain} \times PW_{stim}$, wherein $PW_{stimcor}$ represents stimulation corrected pulse width and $PW_{stim}$ represents the baseline stimulation pulse width.

Optionally, the corrected stimulation may include other corrected stimulation levels/amplitudes and/or pulse widths. For example, a Lapicque relationship may be used to select the pulse width and amplitude. For the original relationships using the original PWstim and Vstimcorr; the rheobase voltage, Vrheo, can be calculated based on the following equation: $V_{rheo} = V_{stimcorr}/(1+\text{chron}/PW_{stim})$, where chron represents the chronaxie and $PW_{stim}$ represents the baseline pulse width. In general, the chronaxie is known for a typical value width for the tissue (e.g., typically in the range of 0.1 to 0.5 ms.).

Once the rheobase voltage, $V_{rheo}$, is known, a correction pulse width can be determined for any select voltage amplitude based on the following equation for an arbitrary $V_{stim}$: $PW_{stim,new} = \text{chron}/((V_{stim}/V_{rheo})-1)$. The foregoing methods may be used to calculate a correction stimulation energy level, based on the gain and a baseline energy level.

After 318, flow returns to 308, where the process is repeated. The foregoing process of FIG. 3 is iteratively repeated continuously or at a select interval to repeatedly update the SCS therapy. It should be recognize that the foregoing process does not adjust the excitation voltage to a level that evokes an ECAP response that is equal in amplitude to the original ECAP response amplitude that was observed at the sensing electrode prior to lead movement. Instead, the foregoing process recognizes that the sensing electrode has also moved relative to the dorsal column. Therefore, the distance has changed between the sensing electrode and the nerve fibers, for which the ECAP response is measured. As the distance changes between the sensing electrode and the nerve fibers being measured, the amplitude of the sensed ECAP response changes, even though the underlying neural response may remain constant. As an example, assume that at time T1 and at time T2, the nerve fibers emit an ECAP response of X milli-amperes or Y milli-volts. At time T1, the distance between the sensing electrode and the nerve fibers is distance D1, while at time T2, the distance between the sensing electrode and the nerve fibers increases to a larger distance D2 (D2>D1). In this example, even through the ECAP response emitted at the nerve fibers remains constant, the sensed ECAP response as measured at the sensing electrode would decrease from $V_{ecap1}$ to a smaller value for $V_{ecap2}$ ($V_{ecap1} > V_{ecap2}$). In accordance with at least certain situations, if the foregoing process managed the excitation SCS therapy such that the sensed ECAP responses were equal ($V_{ecap1} = V_{ecap2}$) when measured at distances D1 and D2 (where D1>D2), the potential exists that the system would result in over-stimulation for increases in lead-to-spinal cord distances. In accordance with at least certain situations, if the foregoing process managed the excitation SCS therapy such that the sensed ECAP responses were equal ($V_{ecap1} = V_{ecap2}$) when measured at distances D1 and D2 (where D1<D2), the potential exists that the system would result in under-stimulation for decreases in lead-to-spinal cord distance. Instead, the process of FIG. 3 provides non-linear feedback control by adjusting the SCS therapy amplitude in a non-linear relation to changes in the sensed ECAP response.

Optionally, the system and method may be configured to have boundary conditions that limit one or more select parameters of the SCS therapy, such as the current amplitude and pulse width. The parameters of the SCS therapy may be limited within minimum and/or maximum values to prevent loss of therapy or production of harmful side effects, respectively. For instance, stimulation current could be limited to a maximum of 10 milliamperes.

Figure 5:
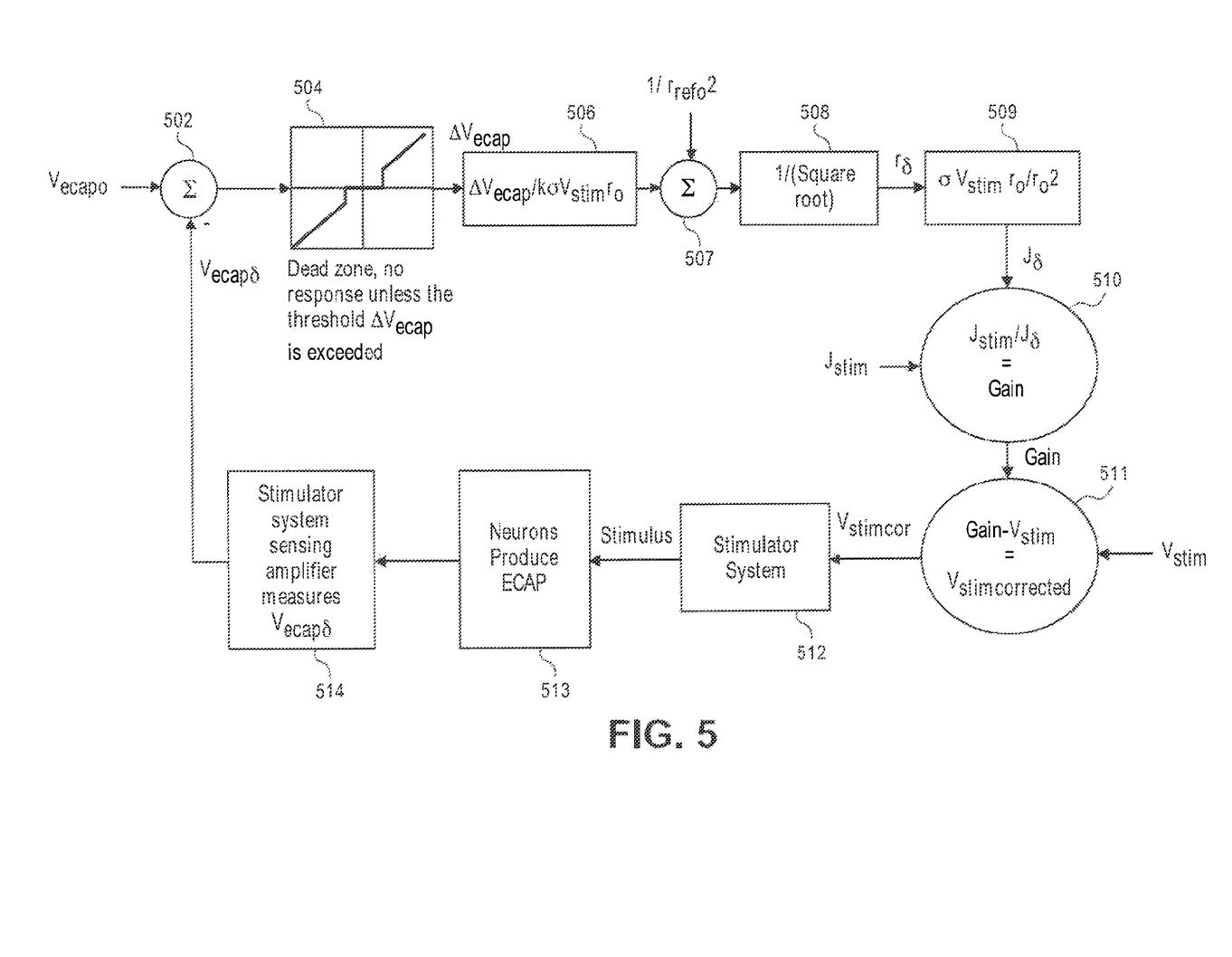
FIG. 5 illustrates a control diagram followed in accordance with embodiments herein when the ECAP response changes.

FIG. 5 illustrates a control diagram followed in accordance with embodiments herein when the ECAP response decreases. The reference ECAP response is $V_{ecapo}$. The upper left shows that $V_{ecap\delta}$ is subtracted at from 502 $V_{ecapo}$. This difference is brought to a dead zone threshold block 504 that has no output unless the difference exceeds a threshold. The ECAP difference $\Delta V_{ecap}$ is brought through modules 506-510 that perform Equations 8-10 above to calculate the increase in stimulus. The generator responds at module 511 by changing the stimulus to $V_{stimcor}$. The excited neurons produce an ECAP at 512-513 that is modulated by the changed stimulus amplitude. This ECAP is detected at 514 by the sense amplifier and the process repeats, closing the loop.

Figure 6:
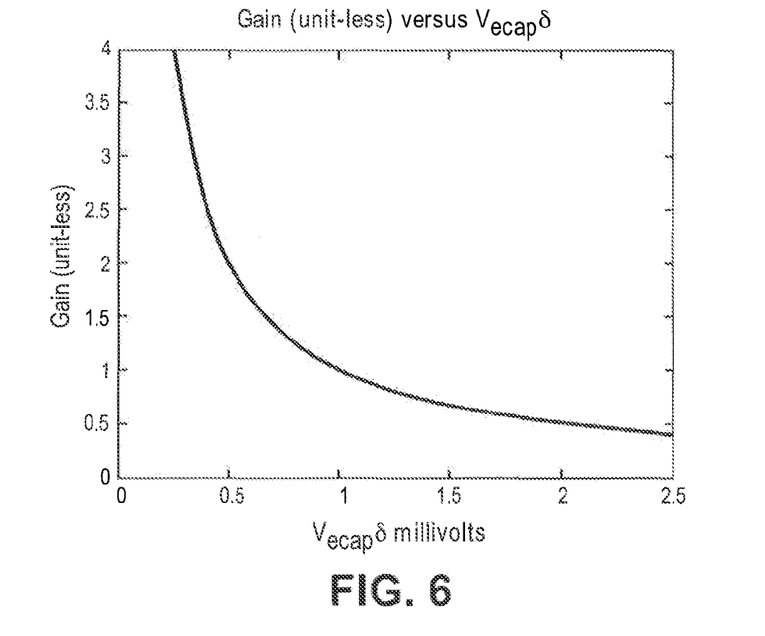
FIG. 6 illustrates a plot of the Gain factor (vertical axis) versus ECAP response amplitude measured after the lead moves to a new position (horizontal axis).

FIG. 6 illustrates a plot of the Gain factor (vertical axis) versus ECAP response amplitude measured after the lead moves to a new position (horizontal axis). The Gain is the factor used to increase the SCS therapy stimulus to compensate for the change in ECAP response. For example, when the measured ECAP response equals the baseline ECAP response, the horizontal axis would equal "1". At this point, the Gain would also equal "1". When the ECAP response is reduced to be smaller, relative to the baseline ECAP response (e.g., when the electrode is moved further away from the nerve fibers at the target tissue site), the gain is increased (e.g., to 1.5, 2.5, and up) such that the SCS therapy stimulation becomes larger until the current flux density at the target tissue site returns to the original (or within a range of the original current flux density). Conversely, when the ECAP response increases to be larger, relative to the baseline ECAP response (e.g., when the electrode is moved closer to the nerve fibers at the target tissue site), the gain is decreased (e.g., 0.75, 0.5 and down) such that the SCS therapy stimulation becomes smaller until the current flux density at the target tissue site returns to the original (or within a range of the original current flux density). The Gain changes in a non-linear relation to change in ECAP response.

Figure 7:
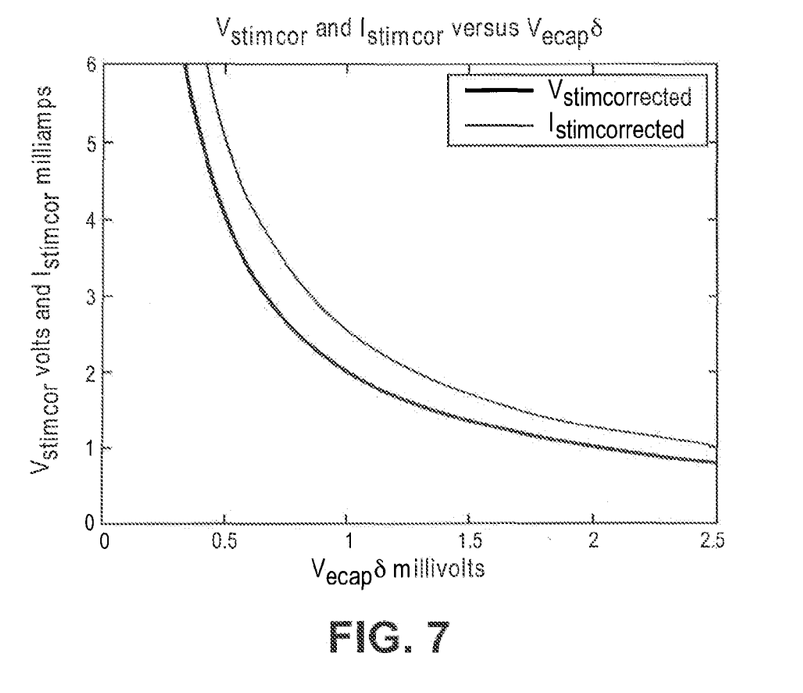
FIG. 7 illustrates a plot of corrected stimulus amplitude (vertical axis), in volts and in milliamps, versus ECAP response amplitude measured after a lead has moved to a new position (horizontal axis).

FIG. 7 illustrates a plot of corrected stimulus amplitude (vertical axis), in volts and in milliamps, versus ECAP response amplitude measured after a lead has moved to a new position (horizontal axis). It is noted that the level of the SCS therapy stimulus goes up substantially when the nerve fibers are relatively far away from the excitation electrode (corresponding to a small ECAP response amplitude). The relation between change in the level of excitation SCS therapy stimulus and the ECAP response is non-linear. Hence, if the level of the excitation stimulus were changed linearly with change in the ECAP response, such an adjustment would potentially lead to an undesirable amount of paresthesia for a select coverage zone.

Figure 8:
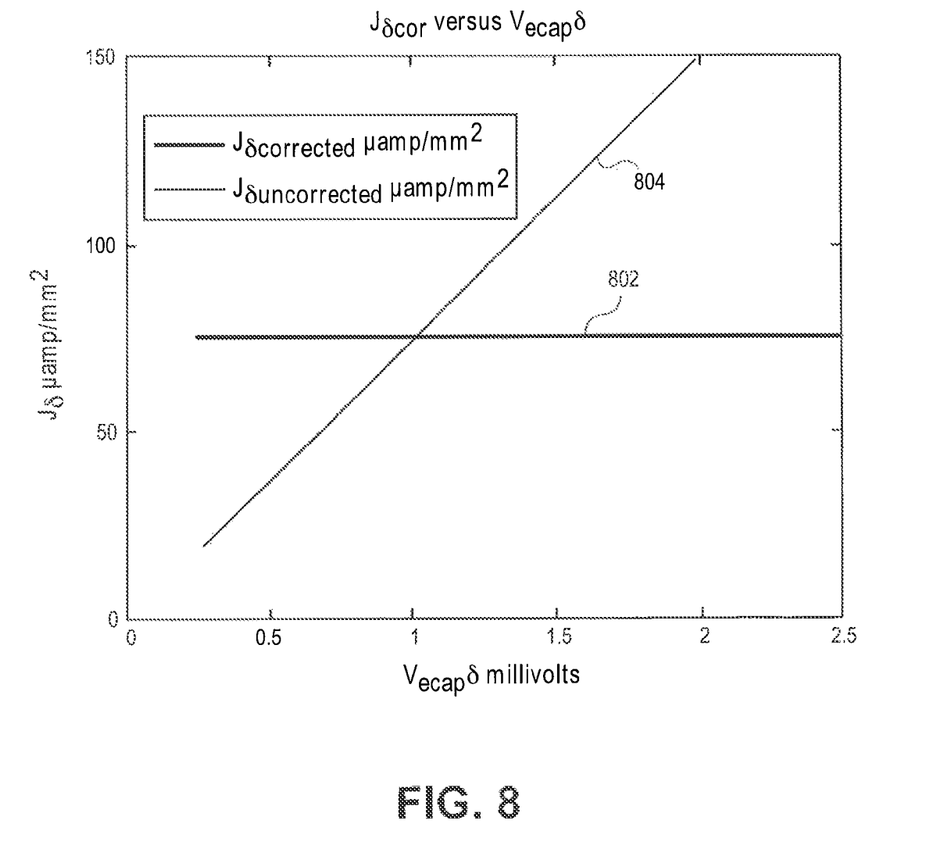
FIG. 8 illustrates a plot of the current flux density (vertical axis) at the nerve fibers versus ECAP amplitude measured after the lead moved to a new position (horizontal axis) in accordance with embodiments herein.

FIG. 8 illustrates a plot of the current flux density (vertical axis) at the nerve fibers versus ECAP amplitude measured after the lead moved to a new position (horizontal axis) in accordance with embodiments herein. Applying the Gain correction factor to adjust the stimulus SCS therapy amplitude, in accordance with embodiments herein, results in stabilization of the current flux density, at 802. Alternatively, if the gain were not adjusted to the change in ECAP amplitude, then the potential exists that the system may under-stimulate when the electrode was far away (small ECAP) and over-stimulate when the electrode was close to the nerve fibers (large ECAP) as shown by graph 804.

Figure 9:
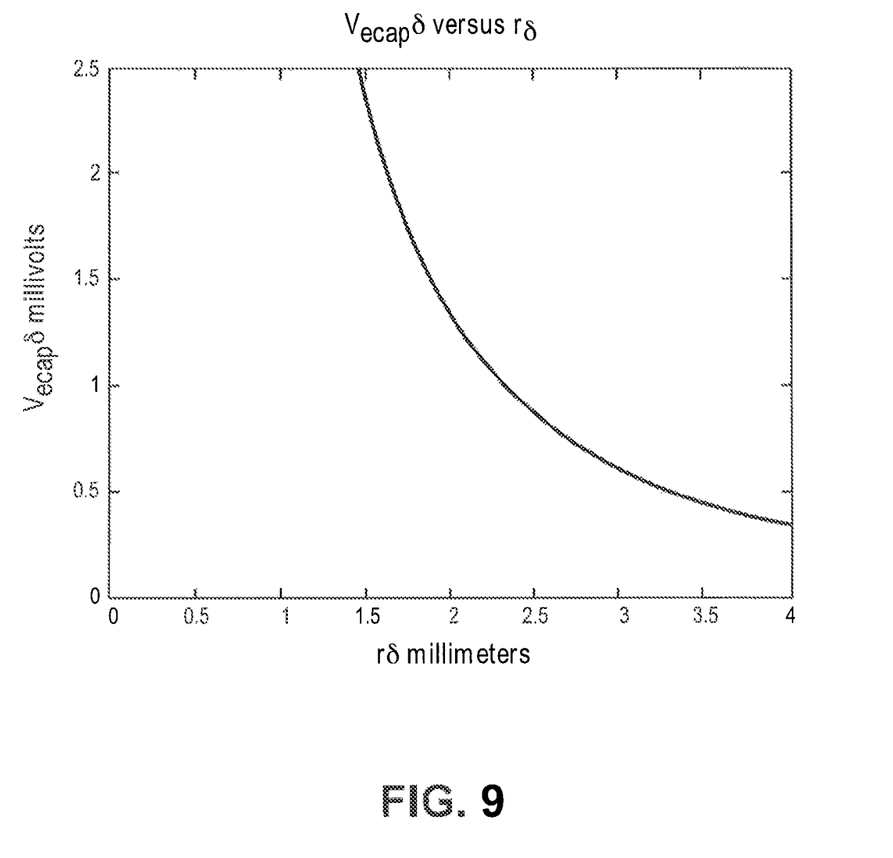
FIG. 9 illustrates a graph showing the ECAP amplitude (vertical axis) is non-linear with the distance (horizontal axis) between the nerve fibers and electrode surface, dropping off very dramatically as the electrode moves away from the nerve fibers.

FIG. 9 illustrates a graph showing the ECAP amplitude (vertical axis) is non-linear with the distance (horizontal axis) between the nerve fibers and electrode surface, dropping off very dramatically as the electrode moves away from the nerve fibers.

The example of FIGS. 4A and 4B is provided in connection with a hemispheric electrode of radius, $r_o$, and for a conductivity, $\alpha$, surrounding the electrode. Optionally, similar solutions may be derived for any electrode geometry. The embodiment described herein in connection with FIG. 3 uses the spherical coordinate solution of the Laplace equation and is chosen for illustrative purposes. Further, the example of FIGS. 4A and 4B may assume a substantially homogeneous isotropic tissue conductivity. When tissue conductivity is non-homogenous, the tissue conductivity is adjusted accordingly.

In other embodiments, the resulting solution will differ for alternative electrode contact shapes, such as cylinders or disks. Additionally, the relation between excitation SCS therapy, current flux density, and sensed ECAP response may change when correction is provided for action potential propagation in extracellular recording and/or assumes a bipolar transmembrane current source in the calculation of $V_{ecapo}$. Other refinements include using appropriate conductivities for cerebral spinal fluid (around 1538 μsiemens/mm), connective tissue (235 μsiemens/mm), and the anisotropic conductivity of the dorsal column (transverse 83 μsiemens/mm and longitudinal 472-775 μsiemens/mm).

Figure 10:
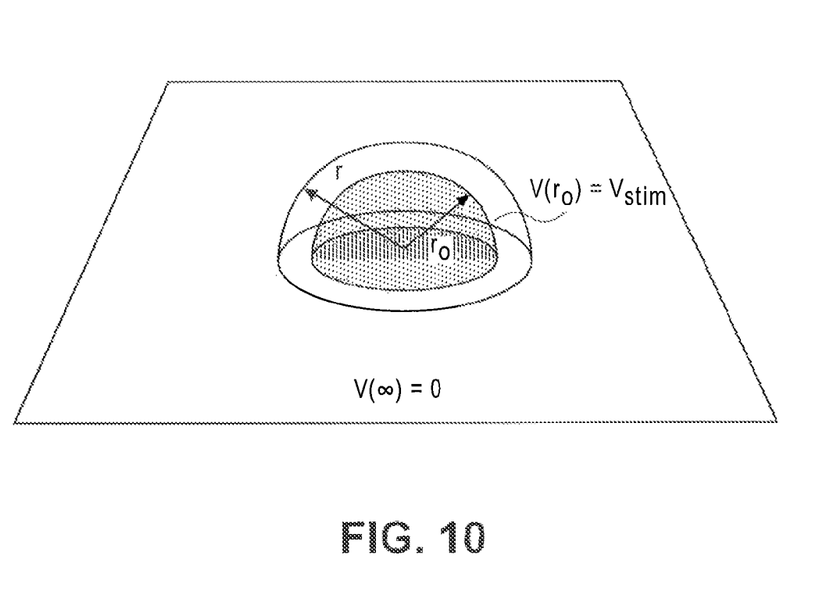
FIG. 10 illustrates a representation of a relevant geometry for the hemispherical solution of a Laplace equation that may be utilized to understand propagation of excitation energy to or from an electrode surface.

FIG. 10 illustrates a representation of a relevant geometry for the hemispherical solution of a Laplace equation that may be utilized to understand propagation of excitation energy from an electrode surface. The surface of the electrode is at $r_o$. The electrode has an electrical potential of $V_{stim}$. The surface defined by the outer sphere at a distance (r) away from the center of the electrode represents the excitable tissue. For the purpose of this example, it may be assumed that the dorsal column of the spinal cord is located as distances greater than r. Far away from the surface of the electrode (e.g., at infinity) the potential is zero volts. The following Laplace transform may be utilized.

$$\nabla^2 V = 0$$

$$\text{Spherical: } \frac{1}{r^2}\frac{\partial}{\partial r}\left(r^2\frac{\partial V}{\partial r}\right) + \frac{1}{r^2\sin\theta}\frac{\partial}{\partial \theta}\left(\sin\theta\frac{\partial V}{\partial \theta}\right) + \frac{1}{r^2\sin^2\phi}\left(\frac{\partial^2 V}{\partial \phi^2}\right) = 0 \quad 12)$$

$$\text{Symmetry: } \frac{\partial V}{\partial \theta} = 0 \text{ and } \frac{\partial V}{\partial \phi} = 0 \text{ thus } \frac{1}{r^2}\frac{\partial}{\partial r}\left(r^2\frac{\partial V}{\partial r}\right) = 0 \quad 13)$$

$$\frac{1}{r^2}\frac{\partial}{\partial r}\left(r^2\frac{\partial V}{\partial r}\right) = 0 \quad 14)$$

$$\text{take derivative } \frac{2r}{r^2}\left(\frac{\partial V}{\partial r}\right) + \frac{1}{r^2}\left(r^2\frac{\partial^2 V}{\partial r^2}\right) = \quad 15)$$

$$0 \text{ and simplify } \frac{2}{r}\left(\frac{\partial V}{\partial r}\right) + \frac{\partial^2 V}{\partial r^2} = 0$$

Equation 12 represents the Laplace equation in spherical coordinates. Equation 13 simplifies Equation 12 by symmetry. Equation 14 is the simplified version of Equation 12. Equation 15 takes the derivative of Equation 14 and simplifies the derivative.

$$\text{Note } \frac{\partial V}{\partial r} = E \text{ therefore } \frac{2}{r}E + \frac{\partial E}{\partial r} = 0 \quad 16)$$

$$2\frac{\partial r}{r} + \frac{\partial E}{E} = 0 \quad 17)$$

$$\text{integrate 6, } \ln E = -2 \cdot \ln r + c_1 \quad 18)$$

$$e^{\ln E} = e^{\ln c_1} \cdot e^{\ln r^{-2}} \quad 19)$$

$$E = \frac{c_1}{r^2} \quad 20)$$

$$\int \partial V = \int E \cdot \partial r + c_2; \text{ integrating } E; \int \partial V = \int \frac{c_1}{r^2}\partial r + c_2 \quad 21)$$

$$V = \frac{c_1}{r} + c_2 \quad 22)$$

$$V(\infty) = 0 = c_2; \text{ therefore } c_2 = 0 \quad 23)$$

$$V(r_o) = \frac{c_1}{r_o} = V_o; c_1 = V_o r_o \quad 24)$$

$$V(r) = V_o \frac{r_o}{r} \text{ and } E(r) = V_o \frac{r_o}{r^2} \quad 25)$$

for $r_o \leq r \leq \infty$

Equation 16 substitutes ∂V/∂r=E into Equation 15 where E is the electric field and results in Equation 12. Next, integrating Equation 12 yields Equation 18. Thereafter, Equation 19 raises Equation 18 to a power of e. Finally, Equation 20 results because $e^{ln\ x}=x$. From the foregoing, it is shown that the electric field is inversely related to $r^2$. Equation 21 integrates the electric field, E, to get the electrical potential, V, which is inversely related to r (See Equation 22). Equation 23 defines the boundary condition at infinity to be $V(\infty)=0$ so $c_2=0$. Finally, Equation 24 applies the boundary condition at the surface of the electrode where $r=r_o$ and $V=V_o$. Therefore, $c_1=V_o$. Finally, Equation 25 defines V and E.

$$J = \sigma \cdot E \text{ and } E(r) = V_o \frac{r_o}{r^2} \text{ so } J = \sigma V_o \frac{r_o}{r^2} \quad (26)$$

$$I = \oint J \cdot ds = \sigma \cdot \oint E \cdot ds = \sigma \cdot V_o \frac{r_o}{r^2} \cdot (2\pi r^2) \quad (27)$$

since $2\pi r^2$ is the area of a hemisphere $$\text{Conductivity} = \frac{I}{V_o} = \sigma \cdot r_o \cdot 2\pi \quad (28)$$

$$\text{By definition, since } R = \frac{V_o}{I} = \frac{1}{\sigma \cdot r_o \cdot 2\pi} \quad (29)$$

Equation 26 defines the current flux density, J. Equation 27 integrates the current flux density over the surface of a hemisphere to get the current, I. In Equation 28, the conductivity is calculated as $I/V_o$ from Equation 27. Finally the electrode stimulation resistance is computed in Equation 29 as $R=V_o/I$.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A system to provide feedback control for spinal cord stimulation, the system comprising:
   a lead adapted to be implanted within an epidural space of a dorsal column of a patient's spine;
   a pulse generator (PG) electrically coupled to the lead, the PG configured to deliver spinal cord stimulation (SCS) therapy;
   sensing circuitry configured to sense an evoked compound action potential (ECAP) response that propagates along the neural pathway; and
   a processor programmed to operation, in response to instructions stored on a non-transient computer-readable medium, to:
      obtain a baseline ECAP response when the lead and spinal cord tissue properties are in baseline states;
      analyze ECAP responses relative to the baseline ECAP response to obtain an ECAP feedback difference indicative of a change in at least one of the baseline state of the lead and the baseline state of the spinal cord tissue properties; and
   adjust an SCS therapy based on the ECAP feedback difference, wherein the SCS therapy creates current flux density (CFD) at nerve fibers within a target tissue site along the neural pathway, and wherein the processor is configured to utilize the ECAP feedback difference to adjust the SCS therapy to maintain a select CFD level at the target tissue site.

2. The system of claim 1, wherein the lead further comprises one or more sensing electrodes and one or more stimulation electrodes, the sensing electrode coupled to the sensing circuitry, the stimulation electrode coupled to the PG, the sensing and stimulation electrodes including at least one of a common electrode, distinct electrodes and partially overlapping electrodes, and wherein a level of the CFD induced onto the nerve fibers at the target tissue site is based on a distance between the nerve fibers and the stimulation electrode(s) and a level of energy emitted at the stimulation electrode(s).

3. The system of claim 1, wherein the processor is configured to undergo an initial calibration process by tuning a constant that includes at least one of the baseline ECAP response, a baseline SCS therapy, and a baseline CFD, associated with a therapeutic level sufficient to create a select patient paresthesia coverage.

4. The system of claim 1, wherein the lead further comprises one or more electrodes, and wherein the processor is configured to determine, as part of a baseline SCS therapy, electrode(s) to deliver SCS therapy, a pulse sequence in the SCS therapy, and a morphology for the pulses within the pulse sequence, the morphology including at least one of an amplitude of pulses, pulse width, a number of pulses in a series of pulses, and a pulse delivery rate.

5. The system of claim 1, wherein a level of the CFD induced onto the nerve fibers at the target tissue site is based in part on at least one of i) a distance between the nerve fibers and excitation electrodes, or ii) a level of energy emitted at the excitation electrode, the processor further configured to utilize the ECAP feedback difference to adjust the SCS therapy to maintain a select CFD level within a select limit of a baseline CFD at the target tissue site.

6. The system of claim 1, wherein a linear relation exists between an amount of current flux density, Jstim, experienced by a bundle of nerve fibers, and a level of an ECAP response, Vecap, that is sensed along a common bundle of nerve fibers, the processor configured to adjust the SCS therapy based on the linear relation.

7. The system of claim 1, wherein the lead further comprises one or more electrodes, and wherein, when the lead shifts in a radial direction toward or away from the spinal cord, a current flux density at the target tissue site changes and in response thereto the ECAP response changes, the processor configured to utilize the change in the ECAP response to calculate information representative of a new distance between the target tissue site to be excited and the electrode.

8. The system of claim 1, wherein the processor is configured to adjust a stimulation parameter of the SCS therapy in a non-linear relation to changes in the ECAP responses sensed.

9. A system to provide feedback control for spinal cord stimulation, the system comprising:
   a lead adapted to be implanted within an epidural space of a dorsal column of a patient's spine;

a pulse generator (PG) electrically coupled to the lead, the PG configured to deliver spinal cord stimulation (SCS) therapy;

sensing circuitry configured to sense an evoked compound action potential (ECAP) response that propagates along the neural pathway; and a processor programmed to operation, in response to instructions stored on a non-transient computer-readable medium, to:
obtain a baseline ECAP response when the lead and spinal cord tissue properties are in baseline states;
analyze ECAP responses relative to the baseline ECAP response to obtain an ECAP feedback difference indicative of a change in at least one of the baseline state of the lead and the baseline state of the spinal cord tissue properties; and
adjust an SCS therapy based on the ECAP feedback difference, wherein the processor is configured to adjust a gain of the SCS therapy in accordance with a non-linear relation relative to changes in the baseline state of at least one of the lead or spinal cord tissue.

10. The system of claim 1, wherein the baseline ECAP response is induced by a baseline current flux density when the lead is in the baseline state, the baseline state representing a baseline distance between the lead and the dorsal column.

11. The system of claim 1, wherein the change in the spinal cord tissue (SCT) properties represents a change in at least one of i) electrical conductivity, ii) thickness of the cerebral spinal fluid layer, iii) fluid status within the cerebral spinal fluid, or iv) tissue composition between lead and spinal column.

12. The system of claim 1, wherein the processor is programmed to adjust the SCS therapy such that the current flux density (CFD) at the target tissue site remains within a select CFD limit relative to a baseline CFD associated with the SCS therapy delivered when the lead is in the baseline state.

13. A method to provide feedback control for spinal cord stimulation from a lead adapted to be implanted within an epidural space of a dorsal column of a patient's spine, the method comprising:
delivering spinal cord stimulation (SCS) therapy to a target tissue site;
sensing an evoked compound action potential (ECAP) response that propagates along the neural pathway;
obtaining a baseline ECAP response when the lead and spinal cord tissue properties are in a baseline state;
analyzing ECAP responses relative to the baseline ECAP response to obtain an ECAP feedback difference indicative of a change in at least one of the baseline state of the lead and the baseline state of the spinal cord tissue properties; and
adjusting an SCS therapy based on the ECAP feedback difference, wherein the SCS therapy creates a current flux density (CFD) at nerve fibers within a target tissue site along the neural pathway, wherein a level of the CFD induced onto the nerve fibers at the target tissue site is based in part on at least one of i) a distance between the nerve fibers and one or more excitation electrodes, or ii) a level of energy emitted at the excitation electrode(s), and wherein the analyzing and adjusting operations use the ECAP feedback difference to adjust the SCS therapy to maintain a select CFD level at the target tissue site.

14. The method of claim 13, further comprising performing an initial calibration process by tuning a constant that includes at least one of the baseline ECAP response, a baseline SCS therapy, and a baseline CFD, associated with a therapeutic level sufficient to create a select patient paresthesia coverage.

15. The method of claim 13, further comprising determining, as part of a baseline SCS therapy, electrode(s) to deliver SCS therapy, a pulse sequence in the SCS therapy, and a morphology for the pulses within the pulse sequence, the morphology including at least one of an amplitude of pulses, pulse width, a number of pulses in a series of pulses, and a pulse delivery rate.

16. The method of claim 13, the analyzing and adjusting operations using the ECAP feedback difference to adjust the SCS therapy to maintain a select CFD level within a select limit of a baseline CFD at the target tissue site.

17. The method of claim 13, wherein a linear relation exists between an amount of current flux density, Jstim, experienced by a bundle of nerve fibers, and a level of an ECAP response, Vecap, that is sensed along a common bundle of nerve fibers, the adjusting operation adjusting the SCS therapy based on the linear relation.

18. The method of claim 13, wherein, when the lead shifts in a radial direction toward or away from the spinal cord, the CFD at the target tissue site changes and in response thereto the ECAP response changes, the analyzing operation utilizing the change in the ECAP response to calculate information representative of a new distance between the target tissue site to be excited and the excitation electrode(s).

19. The method of claim 13, wherein the adjusting operation adjusts a stimulation parameter of the SCS therapy in a non-linear relation to changes in the ECAP responses sensed.

20. A method to provide feedback control for spinal cord stimulation from a lead adapted to be implanted within an epidural space of a dorsal column of a patient's spine, the method comprising:
delivering spinal cord stimulation (SCS) therapy to a target tissue site;
sensing an evoked compound action potential (ECAP) response that propagates along the neural pathway;
obtaining a baseline ECAP response when the lead and spinal cord tissue properties are in a baseline state;
analyzing ECAP responses relative to the baseline ECAP response to obtain an ECAP feedback difference indicative of a change in at least one of the baseline state of the lead and the baseline state of the spinal cord tissue properties; and
adjusting an SCS therapy based on the ECAP feedback difference, wherein the adjusting operation adjusts a gain of the SCS therapy in accordance with a non-linear relation relative to changes in the baseline state of at least one of the lead or spinal cord tissue.

21. The method of claim 13, wherein the baseline state for the lead represents a baseline distance between the lead and the dorsal column.

22. The method of claim 13, wherein the adjusting operation adjusts the SCS therapy such that a therapy current flux density (CFD) at the target tissue site remains within a select CFD limit relative to a baseline CFD when the lead and spinal cord tissue properties are in the baseline state.

* * * * *